United States Patent [19]
Lee et al.

[11] Patent Number: 5,314,811
[45] Date of Patent: May 24, 1994

[54] PROCESS FOR CONVERTING LIPID-CONTAINING BACTERIAL CAPSULAR POLYSACCHARIDE INTO LIPID-FREE POLYSACCHARIDE

[75] Inventors: Ann L. Lee; Mark S. Rienstra, both of Lansdale; Walter E. Manger, Harleysville; Robert D. Sitrin, Lafayette Hill, all of Pa.

[73] Assignee: Merck & Co., Inc., Rahway, N.J.

[21] Appl. No.: 909,346

[22] Filed: Jul. 13, 1992

[51] Int. Cl.$^5$ .................... C12P 19/04; C12P 1/04; C12R 1/21
[52] U.S. Cl. ................... 435/101; 435/170; 435/262; 435/280; 536/117; 536/123.1; 424/88; 424/92; 210/601; 210/616; 210/631
[58] Field of Search ............. 435/101, 170, 262, 280; 536/123.1, 117; 210/601, 616, 631; 424/88, 92

[56] References Cited

U.S. PATENT DOCUMENTS

| | | | |
|---|---|---|---|
| 4,459,286 | 7/1984 | Hilleman et al. | 435/101 |
| 4,686,102 | 8/1987 | Ritchey et al. | 435/101 |
| 4,695,624 | 9/1987 | Marburg et al. | 435/101 |
| 4,830,852 | 5/1989 | Marburg et al. | 536/1.11 |
| 4,882,317 | 11/1989 | Marburg et al. | 536/1.11 |
| 4,963,534 | 10/1990 | Calabria et al. | 536/1.11 |
| 5,019,502 | 5/1991 | Rienstra et al. | 435/101 |
| 5,039,610 | 8/1991 | Rienstra et al. | 435/101 |
| 5,045,456 | 9/1991 | Reinstra et al. | 435/101 |

OTHER PUBLICATIONS

Vella, P. P., and Ellis, R. W., Pediatric Res. 29. 10–13 (1991).
Vella, P. P., et al., Pediatrics Supplement 85, 668–675 (1990).
Imamura, S. and Horiuti, Y., J. Biochem. 85, 79–95 (1979).
Jennings, H. J., Proceedings of an Int. Symposium on Mol. Immunol. of complex carbohydrates, Sep. 13–15, 1985, pp. 495–550.
Kuo et al., J. Bacterial 163, 769–773 (1985).
Gotschlich et al., J.B.C. 256, 8915–8921 (1981).
Kates, M. Canadian J. of Biochem & Physiol 35, 127 (1957).
Kates, M. and Gorham, P. R., Canadian J. of Biochem and Physiol 35, 119 (1957).
Rosenberg et al., J.B.C. 236, 2845–2849 (1961).
Zamenhof et al., J.B.C. 203, 695–704 (1953).

Primary Examiner—Ronald W. Griffin
Attorney, Agent, or Firm—Gerard H. Bencen; Jack L. Tribble; Paul D. Matukaitis

[57] ABSTRACT

A process for converting lipid-containing bacterial capsular polysaccharide, such as lipo-polyribosyl ribitol phosphate, lipo-PRP, into lipid-free, endotoxin-free polysaccharide, such as polyribosyl ribitol phosphate, PRP, by solubilizing polysaccharide-containing powder derived from culture media of bacteria, such as *Haemophilus influenzae* type b, cleaving covalently bound fatty acids from the polysaccharide, and removing the lipids, and endotoxin.

14 Claims, 3 Drawing Sheets

PROCESS FOR CONVERTING LIPID-CONTAINING BACTERIAL CAPSULAR POLYSACCHARIDE INTO LIPID-FREE POLYSACCHARIDE

BACKGROUND OF THE INVENTION

The invention is a process for the production of lipid-free, capsular polysaccharide from cultures of bacteria, including type-specific capsular polysaccharide from Gram-negative bacteria, free of endotoxin, without incurring substantial loss of the capsular polysaccharide. The process converts capsular polysaccharide which has covalently bound glycerol diester moieties into lipid free polysaccharide. In a preferred embodiment of the invention, lipopolysaccharides, LPS or endotoxin, is also removed from the capsular polysaccharide from which covalent lipid has been cleaved.

In one embodiment of the invention, the process is adapted to the production of lipid-free polyribosyl ribitol phosphate, hereinafter referred to as PRP, which is the capsular polysaccharide derived from cultures of the pathogenic bacterium *Haemophilus influenzae* type b, also referred to as Hib. The PRP produced is suitable as a component for the preparation of vaccines for induction of immune responses which protect against development of diseases caused by Hib. From this invention, it is predictable that the capsular polysaccharide of other pathogenic bacteria which have a similar covalent lipid, as in *E. coli* or *Neisseria meningitidis*, may be produced in similarly high yield by employing the teaching disclosed herein.

The pathogenic bacterium, Hib, is responsible for a number of diseases, the most significant of which is bacterial meningitis and systemic bacterial disease which occurs primarily in children under 5 years of age. Recently, vaccines directed against Hib have been licensed for use in humans by the FDA, see 1991 Physicians Desk Reference, pp. 1476–1478 for Merck & Co., Inc.'s PedvaxHIB®, and pp. 1174 1176 for Lederle's Hib TITER®.

One method of producing a vaccine against Hib is provided by the process described in U.S. Pat. Nos. 4,695,624 and 4,882,317. The PRP used in that process is derived from culturing *Haemophilus influenzae* type b, and isolating a fraction of polysaccharide from the culture medium. The isolated PRP is then conjugated with the outer membrane protein complex from *Neisseria meningitidis* b which acts as an immune enhacing carrier for the PRP which by itself is poorly immunogenic in infants.

Referring now to U.S. Pat. No. 4,695,624, an 800 L fermentation of *Haemophilus influenzae* type b is concentrated, in column 16, line 24, to 377 g of wet paste. The PRP is recovered by selective precipitation at different ethanol concentrations in the presence of calcium chloride. In column 17, line 1, 68 grams of dry product is obtained, hereinafter referred to as pre-phenol powder. Further workup involves phenol extraction and ethanol precipitation, yielding 39 grams of dry product in column 17, line 49, and then, finally ending up with 34.7 grams of dry product in column 18, line 14. This material will hereinafter be referred to as post-phenol powder. The post-phenol powder may be conjugated or subjected to further purification to remove endotoxin.

Endotoxin is a major contributor to elevation of temperature in mammals upon inoculation with bacterial derived immunogens. This so-called pyrogenic response may be eliminated by removal of lipid A containing lipopolysaccharides, hereinafter referred to synonomously as endotoxin, pyrogen or LPS, from the immunogen. In order to achieve this goal, the post-phenol PRP product obtained above may be further purified so that regulatory standards for pyrogen are met. Until the development of the instant invention, this was achieved by losing about 70% of the PRP present in the post-phenol powder, by selective ethanol fractionation. This involves precipitation of LPS from the post-phenol PRP by addition of ethanol to a sufficient concentration to just initiate precipitation, the so-called cloud point as outlined in U.S. Pat. Nos. 5,039,610 and 5,045,456. Ethanol is added to the cloud point, which is where about a two-fold increase in turbidity is achieved. An additional 0.5–2% ethanol is added, and the precipitate, which was heretofor a waste-product, hereinafter referred to as low-cut, is obtained, while lipid-free PRP remains in solution. Low-cut contains about 70% of the PRP and essentially all of the LPS.

In an attempt to overcome the loss of PRP which results from selective ethanol fractionation for endotoxin removal, the inventors of the process of U.S. Pat. No. 5,019,502 developed a method to remove LPS without substantial loss of PRP. The method involves passage of solubilized post-phenol powder through a hydrophobic adsorption step, either in the batch mode or column chromatographic mode, and preferably using nonionic resins to which endotoxin binds, but to which polysaccharides do not bind.

Use of a resin of highly porous styrene and divinylbenzene copolymer, such as HP20 does indeed quantitatively remove essentially all endotoxin, while providing almost quantitative yield of the PRP. This material is hereinafter referred to as post-HP20 PRP. However, a substantial portion of the PRP produced by Hib is in the form of a covalent lipo-PRP.

The possibility that PRP is produced by *Haemophilus influenzae* type b as lipo-PRP was first recognized by Kuo et al., [*J. Bacteriol.* 163, 769–773 (1985)], wherein *Haemophilus influenzae* type b was grown in a liquid medium supplemented with radioactive palmitate and/or radioactive ribose. The polyribosyl ribitol phosphate purified from the culture supernatant contained both radioactive ribose and palmitate which had been incorporated into the PRP during biosynthesis. Phospholipase $A_2$ (PLA$_2$) treatment was shown to remove some of the radioactive palmitate from the PRP whereas methods that would disrupt noncovalent association were unsuccessful. A structure for lipo-PRP was not given, but the data presented was consistent with the data reported in an earlier publication which proposed a structure for the meningicoccal group A, B, C and *E Coli* K92 polysaccharides [Gotschlich et al., *J. Biol. Chem.* 25b, 8915–8921 (1981)]. In the present invention, work with specific phospholipases has revealed a structure for lipo-PRP which is consistent with that presented in the detailed description below.

Lipo-PRP does not bind to the hydrophobic resin used in the U.S. Pat. No. 5,019,502 invention, due to the minor hydrophobic nature conferred on lipo-PRP by the covalent lipids, as opposed to the overwhelmingly anionic nature of the very large polysaccharide portion of the molecule. Thus, the final product obtained from that process contained a substantial portion of lipo-PRP as well as lipid-free PRP. This lipo PRP is removed, either by selective ethanol fractionation, which incurs about a 70% loss of PRP, or by employing the process deisclosed herein, whereby essentially all of the PRP is recovered as lipid-free PRP.

Thus, an object of this invention is to provide a process for recovery of lipo-free capsular polysaccharide such that a conjugate product is produced that is indistinguishable from conjugate prepared using only that fraction of lipid-free polysaccharide obtained by selective alcohol fractionation. Another object of this invention is to provide a process for high-yield production of PRP which comprises conversion of lipo-PRP into lipo-free PRP, rather than discarding the lipo-PRP. Another object is to provide a process which is reproducible for the amount and consistency of PRP obtainable from cultures of Haemophilus influenzae type b to ensure consistency of conjugate vaccine produced with the PRP so produced. Other advantages and objects of the invention will become apparent from the complete description as follows.

SUMMARY OF THE INVENTION

A process for preparing capsular polysaccharide from bacteria, including type-specific capsular polysaccharide from Gram-negative bacteria, which comprises converting the capsular polysaccharide which has covalent attachments to lipid, into lipid-free capsular polysaccharide and removing endotoxin contaminants. In a preferred embodiment, lipo-PRP is converted into lipo-free-PRP by treatment of a crude or purified preparation of PRP derived from a culture of Haemophilus influenzae type b by cleaving the covalent lipids from PRP with phospholipase D in a buffer containing about 50% by volume of organic enzyme activators, about 0.3% detergent, and about 5 mM divalent metal cation, at about 35° C. and about neutral pH, for about 30 minutes to about 4 hours, followed by removal of the enzyme, residual lipids and lipopolysaccharides.

DETAILED DESCRIPTION OF THE INVENTION

This invention is a process for cleaving covalently bound lipid from bacterial capsular polysaccharide and removing the lipid and endotoxin contaminants. Chemical, or enzymatic means for removing the lipid may be utilized. Selective ethanol fractionation of polysaccharide having covalently bound lipid results in loss of that fraction of capsular polysaccharide as a waste-product termed "low-cut". By effecting removal of covalently bound lipid, the instant process avoids the loss of capsular polysaccharide incurred by selective alcohol fractionation, while providing a polysaccharide product which is useful for the preparation of a free or conjugated polysaccharide vaccine to protect against infection by the pathogen from which the polysaccharide is derived. Covalent lipid may be removed by treatment with, for example, hydroxylamine. The preferred method for cleaving the covalent lipid from the capsular polysaccharide is enzymatic. In a preferred embodiment of the invention, high yield production of polyribosyl ribitol phosphate, PRP, is achieved (the enhanced PRP process).

Figure 1:
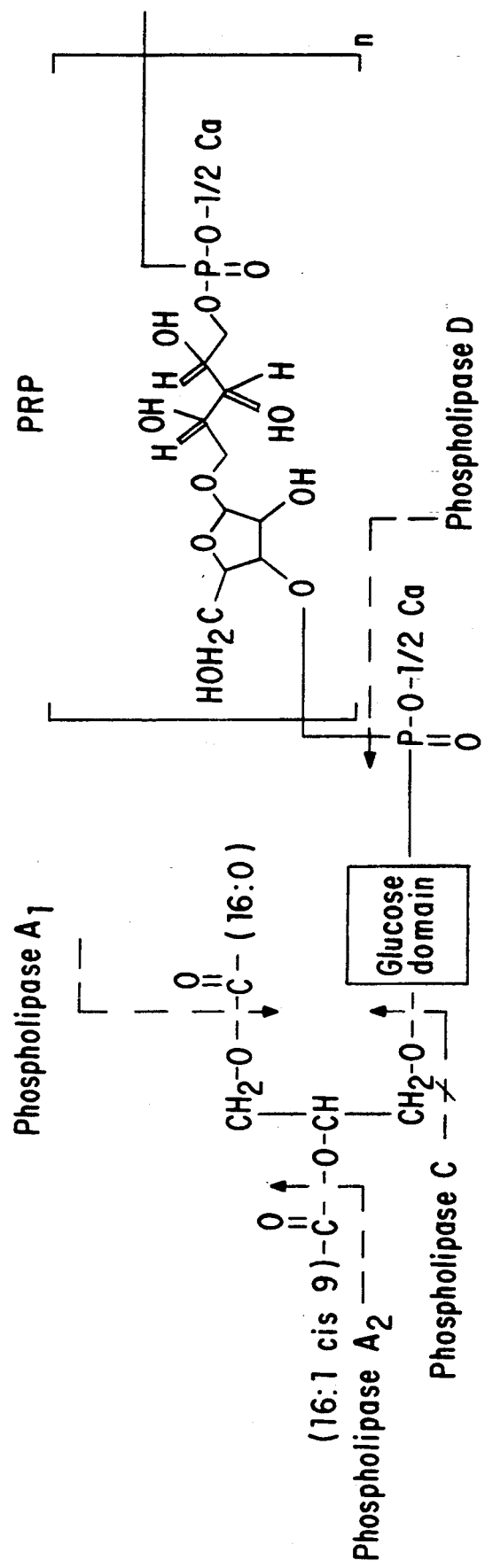
FIG. 1. Proposed structure of lipo-PRP.
Figure 2:
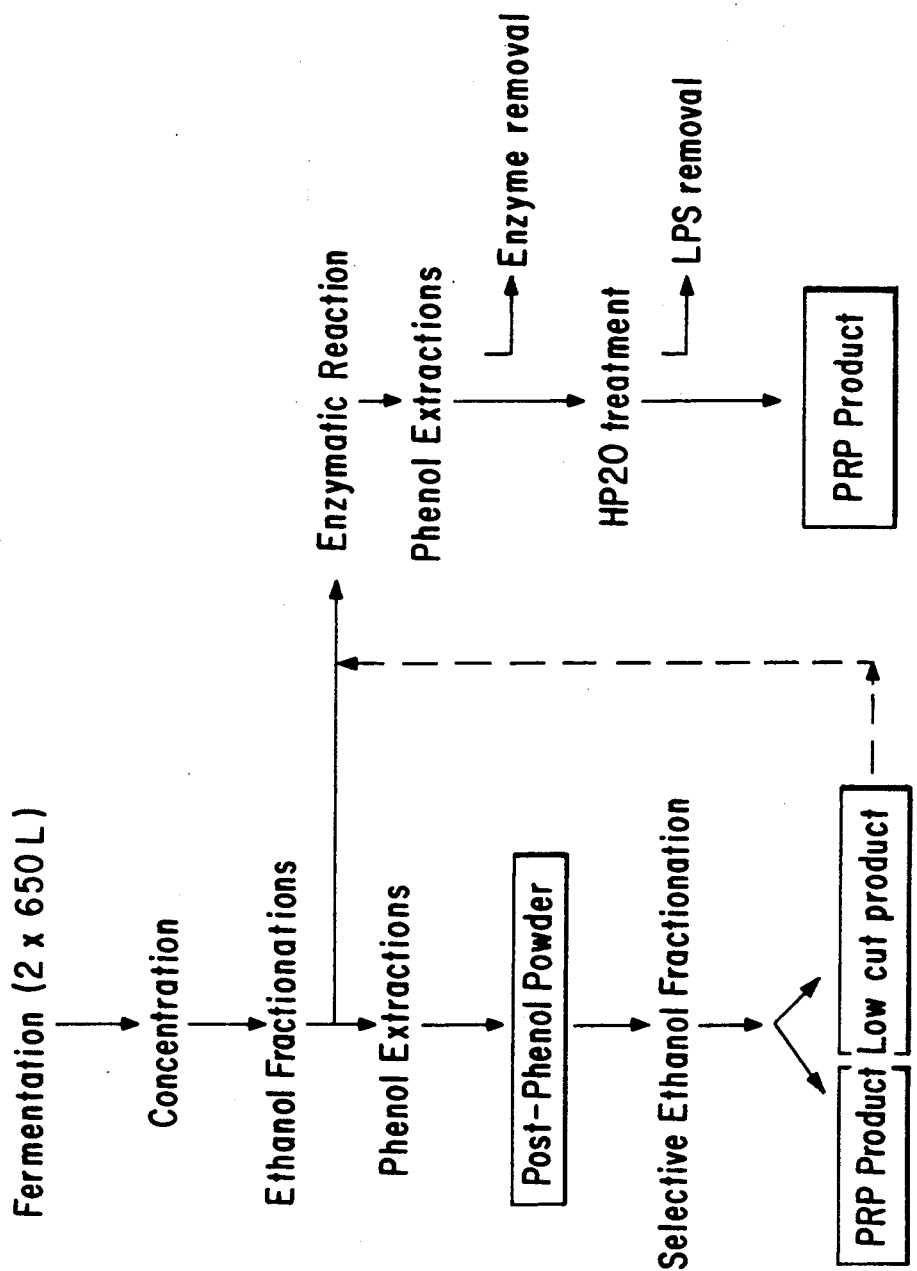
FIG. 2. Comparison of PRP production using selective alcohol fractionation and PRP production using enzymatic conversion of lipo-PRP to PRP followed by enzyme removal and LPS removal.

The process of this invention may be understood with reference to FIG. 1. A proposed structure for lipo-PRP is shown, based on studies with phospholipases of defined specificity. The structure of lipid-free PRP is the same as that shown in FIG. 1 except that no diacylglycerol moiety is esterified to the phosphate of the PRP repeat unit. In addition, the presence in lipo-PRP of glycerol has been confirmed by Dionex HPLC, and the presence of glucose has also been confirmed.

Phospholipase $A_2$ ($PLA_2$) is known to cleave at the indicated sn-2 position of diacylglycerols. When PRP is reacted with a preparation of commercially available $PLA_2$ (Sigma, Boehringer) and the release of fatty acids is monitored by gas chromatographic analysis, a reduction in palmitoleic acid [16:1 cis 9] but not of palmitic acid [16:1] or myristic acid [14:0], all of which are detected in lipo-PRP, is noted.

Commercially available phospholipase B (Sigma) was able to remove some fraction of palmitic and palmitoleic acids, but the glucose and glycerol are not removed by this enzyme. Furthermore, the activity of phospholipase C (Sigma) appeared to be blocked and therefore the position of glucose is as assigned in FIG. 1. Commercially available phospholipase D (Sigma, Genencor, Boehringer) removes all the fatty acid, as well as the glycerol and glucose. However, none of these enzymes could initially be used alone, and none of the enzymes removed 100% of the fatty acids from PRP prior to optimization of the instant process. The instant invention provides an optimized process for achieving complete lipid removal using PLD alone. In addition, however, combinations of PLD and $PLA_2$ or PLB could also be used to advantage in the removal of covalent lipids. In one embodiment of the invention, phospholipase $A_2$ and phospholipase D are used in combination at ambient temperature to completely remove covalent lipid from lipo-PRP, and subsequent conjugation of the lipid-free PRP product with an immunogenic protein is shown to be efficacious in raising strong anti-PRP immune responses.

Reductions in phospholipase requirements are desirable since these enzymes are costly, and because a reduced enzyme load facilitates the enzymes' removal from the product. Complete fatty acid removal from post-phenol powder PRP can be achieved using 700 U of phospholipase $A_2$ (from porcine) and 20 U phospholipase D (from Streptomyces chromofuscus), along with 30% butyl ether and 0.1% DOC which are potent enzyme stimulators. It has been described in the literature that phospholipases and similar enzymes are extremely sensitive to reaction additives such as detergents and organic solvents. In particular, Kates showed that plastid phosphatidase C was greatly stimulated by the addition of ether-methanol mixtures, which are believed to interact synergistically to allow substrate and enzyme phases to coalesce in a region of enhanced enzyme activity, [Can. J. Biochem. and Physio, 35, 127 (1957)]. We suspected that a similar mechanism might govern phospholipase activity and therefore investigated the effect of ether-methanol mixtures on enzyme performance.

A butyl-ether/methanol mixture proved to be a very potent activator for the phospholipase reaction. A scheme consisting of reacting post phenol PRP powder with $PLA_2$ and PLD in the presence of a 5-to-1 (v/v) mixture of butyl-ether and methanol, followed by treatment with HP20 resin to reduce endotoxin, resulted in complete removal of lipids from the PRP. Moreover, the enzyme requirements were reduced 3.5-fold for the $PLA_2$ (from 700 U to 200 U) and 2-fold for phospholipase D (from 20 U to 10 U). An additional advantage of employing the HP20 treatment after the enzyme reaction is that the hydrophobic resin adsorbs some of the enzyme from the reaction mixture, thus easing the burden of downstream enzyme clearance.

In view of the desire to prepare a vaccine for human administration, it is desirable to use as little enzyme as possible, to remove the enzyme totally or as near as totally as possible, and to use an enzyme derived from a source that has no possibility of contamination with mammalian viruses. The use of porcine $PLA_2$ may be undesirable since there can be an increased risk of an unwanted immunological response and there are recent fears of undetectable viruses in mammalian derived products. $PLA_2$ isolated from *Streptomyces violaceoruber* was evaluated under the same reaction conditions described above. The lipids were successfully removed using a combination of the phospholipases from Streptomyces. Additional experiments were carried out in order to determine that the minimum enzyme requirements for 100 mg PRP were between 100 and 200 U for Streptomyces $PLA_2$ and between 2 and 10 U for PLD.

It should be noted that many different sources for the enzymes designated as phospholipase $A_2$, D, or B exist. Snake venoms are rich sources of $PLA_2$, while PLD has been isolated from cabbage, peanut, and Streptomyces. Choice of a particular source is largely dictated by the concerns noted above and by the specific activity of the commercially available enzyme preparations. Furthermore, it is possible that other lipases could ex Hib it sufficient secondary phospholipase-like activity to make them useful for our application. Application of these other lipases for this purpose should be obvious from this invention.

The enzymatic methods using either the combination of phospholipases or phospholipase D alone to cleave lipids from post-phenol powder PRP have been shown to be very reproducible and capable of accommodating the variability of lipid content between phenol and thimerosal inactivated cultures of *Haemophilus influenzae* b. In addition, when the enzymatic reaction is followed by HP20 treatment, the pyrogen is significantly reduced from 60 EU/mcg in the post phenol PRP starting powder, to about 10 EU/mcg after enzymatic reaction, down to 0.0125 EU/mcg following HP20 treatment. This appears to be an excellent scheme for ensuring complete lipid removal, significant reduction of LPS and high PRP recovery. Other schemes are, of course, possible, such as inclusion of the lipase earlier in the PRP isolation process, such as in the fermentation broth, or immediately after killing the bacteria. Also, alterations in the order in which the various steps are performed naturally fall within this disclosure.

In a preferred embodiment of the invention, the enzymatic removal of all lipid from lipo-PRP is achieved in an optimized reaction which comprises reacting the PRP with only phospholipase D derived from *Streptomyces chromofuscus* at a ratio of about 0.3 weight percent of phospholipase D to PRP. This enzyme was purified to homogeneity by Imamura and Horiuti [J. Biochem. 85, 79–95 (1979)], and is commercially available through Genencor International, but as noted above other sources of PLD may be used.

Optimized conditions for PLD, include addition of Triton X-100 which appears to be a more effective enzyme activator than deoxycholate, DOC. In addition, the activity of the enzyme is also sensitive to the amount of $Ca^{2+}$. To increase the activity of the enzyme, 4.5 mM Triton X-100 and $Ca^{2+}$ (5 mM) was added, although other divalent metal cations, such as magnesium, may be used. The addition of calcium in the reaction mixture gives rise to the need to use a buffer other than phosphate, such as 10 mM Tris at pH 7.4. The amount of organic solvents added to the reaction mixture was increased to 50% v/v, and the butyl-ether was replaced with methyl-tert-butyl-ether which reduces safety concerns. Using these modified enzyme reaction conditions and followed by HP20 treatment, complete removal of the lipid from the pre-phenol powder PRP was achieved. The reactions were repeated on 2 grams each of two different batches of pre-phenol powder PRP to show the reproducibility and effectiveness of PLD treatment on pre-phenol powder PRP. The lipid-free products were assayed for molecular size determination by Sepharose CL4B chromatography. The Kd of the products were about 0.4–0.5 which is acceptable for PRP immunogenicity. Naturally, other buffer conditions or similar detergents may be used in the reaction, as would be appreciated by those skilled in the art.

The Enhanced PRP Process was demonstrated in triplicate in the Haemophilus b Conjugate Vaccine (Meningococcal Protein Conjugate) manufacturing facility. Six phenol-inactivated *H. influenzae* fermentation lots were used in the consistency series. The fermentation lots were tested for culture purity, *H. influenzae* inactivation and PRP antigen content and the results were all satisfactory. Three manufacturing lots of PRP were prepared and subsequently used as starting materials for the preparation of three full-scale lots of Haemophilus b Conjugate Vaccine (Meningococcal Protein Conjugate). The product recovery yields for three lots of PRP, each starting from two fermentation cultures, was about 3.5 times higher than yields using selective ethanol fractionation.

Three lots of PRP prepared by the Enhanced Process were subsequently used in the manufacture of Haemophilus b Conjugate Vaccine (Meningococcal Protein Conjugate). Release testing of the derivatized Haemophilus b polysaccharide bulk, the Haemophilus b (PRP-OMPC) conjugate bulk, and the Haemophilus b Conjugate Vaccine (Meningococcal Protein Conjugate) Final Container, show that these materials are all indistinguishable from similar materials from the selective alcohol fractionation process.

Low-cut PRP is the waste precipitate (containing LPS, lipo-PRP and lost PRP) from selective ethanol fractionation, which is the last step in the PRP production process disclosed in U.S. Pat. No. 5,039,610. Using the same improved reaction conditions that were developed for pre-phenol powder and followed by HP20 treatment, essentially complete removal of the lipid from low-cut powder was effected with greater than 70% PRP yield.

The reaction mixture should contain an organic solvent which activates the phospholipase, and is preferably present at between about 30% and 60% of the reaction volume. The organic activator is preferably an ether such as diethyl ether or methyl-tert-butyl ether. The ether is advantageously provided in admixture with a second organic solvent such as hexane, ethanol, or methanol, in a ratio of ether to second organic of between about 20:1 and 5:1, and a preferred ratio is about 9:1 ether to second organic. In a highly preferred embodiment, 9 parts of methyl-tert butyl ether, which is less volatile than diethyl ether and thus safer to handle, is mixed with about 1 part of ethanol, and this organic mixture is added to the PLD reaction to a final organic concentration of about 50%. The provision of the organic solvent appears to assist in maximal contact of the lipid substrate and the enzyme.

In addition to provision of the organic enzyme activator, it is desirable to provide a detergent, such as deoxycholate or Triton X-100, or a similar detergent, to assist in breaking up lipoidal aggregates and enhance the enzyme-substrate interaction. The detergent should be present at a concentration between about 0.1% and 0.4%. Addition of about 0.3% of Triton X-100 has been found to be quite satisfactory.

Phospholipase D should be provided in a sufficient quantity in relation to the lipo-capsular polysaccharide to achieve complete hydrolysis of covalent lipid within a reasonable period of time. Provision of between about 0.01 and 10% of PLD relative to PRP, and preferably between about 0.1 and 0.4% is suitable. Naturally, addition of less enzyme will require longer reaction times while addition of more enzyme will shorten the reaction time.

Provision of agitation to the reaction to maintain all reaction phases in contact with each other, about 0.1 to 0.4 weight percent PLD, about 0.1 to about 10 mM divalent metal cation, such as $CaCl_2$, in a buffer compatible with all of the aforementioned reagents, such as Tris, at a pH between about 7.0 and 8.0, and a temperature between about 20° C. and 45° C., and preferably between 30°–40° C., allows for complete removal of covalent fatty acids from lipo-PRP within about 30 minutes to 4 hours of reaction time.

The above stated reaction conditions have been found to be quite satisfactory for provision of PRP free of covalent lipid, starting with PRP preparations of vastly different purity. Thus, pre-phenol powder, post-phenol powder, and post HP20 product have all been treated under these conditions and consistent production of PRP free of covalent lipid has been noted.

Further to the conversion of lipo-PRP in a given preparation to free PRP, the phospholipase which is now present in the PRP preparation may be removed by phenol extraction of the proteinaceous enzyme. To ensure complete removal, the phenol extraction is preferably repeated at least once and up to about four extractions. This treatment removes not only the added enzyme, but also any residual proteinaceous contaminants than might interfere with downstream conjugation or provide undesirable immune responses in vaccine recipients.

The enzymatic treatment of the PRP to produce PRP devoid of covalent fatty acids also cleaves some of the fatty acids from LPS. Endotoxin is therefore reduced by about 3-fold as a result of the enzymatic treatment. However, this level of reduction is usually not sufficient to meet pyrogenicity specifications, and further steps are necessary to eliminate residual LPS. Any of a number of means known in the art, including selective ethanol fractionation, hydrophobic adsorption or other methods which are canvassed in the disclosure provided by U.S. Pat. No. 5,019,502, may be employed to further remove the endotoxin. Resins which are useful in the present invention include but are not limited to Borate Avidgel (Amicon), Amberlite XAD and Amberchrome (Rohm & Haas), Octyl Cellulose (Phoenix Chem.), Silica C8 (Baker), SP and HP Series resins (e.g. SP207, HP20, HP50) (Mitsubishi Chem.). Of these resins, HP20 or HP50 is preferred because of lipopolysaccharide reduction, ease of use, availability, cost, and its propensity to avoid binding to polysaccharides. Preferably the resin is washed prior to use with pyrogen free water. More preferably, the resin is washed prior to use with acid solution, an alkali solution, or a polar solvent (e.g. ethanol or methanol) and then with pyrogen free water, and then pre-equilibrated with a buffer consisting of 3% sodium citrate and 0.5% sodium deochycholate. Likewise, the polysaccharide is preferably solubilized in a buffer comprising about 3% sodium citrate and about 0.5% sodium deoxycholate and then treated with the hydrophobic resin prepared as describe above. Addition of about 25 mM Tris pH 8.0 is also useful to prevent pH fluctuation.

The capsular polysaccharide containing covalent lipid may be converted to free polysaccharide either before or after removal of endotoxin. In one embodiment of the invention, a powder derived from H. influenzae b fermentation broth containing polyribosylribitol phosphate, lipopolysaccharides, and various lipids and proteins is solubilized in 10 mM Tris, 5 mM $CaCl_2$, 4.5 mM Triton X-100, pH 7.4, and a 9:1 mixture of tert-butyl ether:ethanol is added to a concentration of 50%. About 0.3 weight percent, as compared to PRP, of phospholipase D from Streptomyces chromofuscus is added, and cleavage of lipids is allowed to occur, with constant agitation, at about 35° C. for about 3 hours. The reaction product is phenol extracted four times to remove proteinaceous contaminants, including added enzyme, to provide a post-phenol sample.

The post-phenol sample is then dissolved in a detergent/chelating agent mixture under basic pH. HP20 resin beads, which have been pre-treated with the same buffer, are added to and mixed with the PRP solution in an orbital shaker for several hours below room temperature. The beads are then removed from the solution by filtration, and the filtrate is diafiltered to remove the detergent and chelating agent. Retentate is recovered and calcium chloride added. The PRP is precipitated from solution with 95% ethanol. The precipitate is centrifuged and the pellet is triturated with ethanol and acetone. The resulting product is vacuum dried.

The process using hydrophobic resin beads results in low levels of contaminating endotoxin without significant loss of PRP. Endotoxin reduction resulting from this treatment is typically 100–21,000 fold between starting and final powder, depending on the initial level of endotoxin contamination. PRP yield is typically at least 75% and sometimes more than 90% of the starting material.

The Limulus Ameobocyte Lysate (LAL) test described in "Guideline on validation of the LAL test as an end-product endotoxin test for human and animal parenteral drugs, biological products, and medical devices". U.S. Department of Health and Human Services, December 1987 is used to determine endotoxin levels.

In a preferred embodiment of this invention, endotoxin-free and lipid-free PRP is provided by following the enzymatic treatment with the hydrophobic adsorption of LPS by HP20 or other suitable porous styrene and divinyldibenzene copolymer or similarly hydrophobic medium, as described above.

The capsular polysaccharide of Gram-negative bacteria is obtained according to any of a number of known methods, including those presented in U.S. Pat. No. 4,695,624 for *Haemophilus influenzae* type b, and the anionic capsular polysaccharides of *Neisseria meningitidis* (meningococcal) groups A, B, C, X, Y, W135 and 29E polysaccharides, and *Escherichia coli* K1, K12, K13, K89, K92 and K100 polysaccharides. Particularly preferred polysaccharides, however, are those capsular polysaccharides selected from the group consisting of Hib polysaccharide, such as described in Rosenberg et al., *J. Biol. Chem.*, 236, pp. 2845-2849 (1961) and Zamenhof et al., *J. Biol. Chem.*, 203, pp. 695-704 (1953). In one embodiment of this invention, polyribosyl ribitol phosphate, which is the capsular polysaccharide from *Haemophilus influenzae* type b, is isolated by fermentation of the pathogen as described in U.S. Pat. No. 4,695,624. The pathogen is killed by addition of 1% thimerosal or addition of about 0.5% phenol. The cell debris is removed by centrifugation, and the crude polysaccharide is concentrated by ultrafiltration, to provide what is hereinafter referred to as crude PRP. The yield of free PRP may be optimized by conversion of lipo-PRP to PRP free of covalent lipid, if the enzymatic treatment is conducted on crude PRP according to the enzymatic method described above, and it may even be advantageous to add the lipase directly to the fermentation medium or at any subsequent step.

For example, the enzyme treatment may be delayed until after partial purification by any of the following treatments, or after part of any of the following treatments, or after any equivalent variant of the following treatments: production of pre-phenol powder by removing contaminants insoluble at 48% ethanol (v/v), addition of ethanol to 61% to recover polysaccharide, resolubilization in about 1M CaCl$_2$ and removal of further contaminants insoluble at 23% ethanol (v/v), followed by PRP recovery at 37% ethanol (v/v), and finally, trituration in absolute ethanol; or after production of post-phenol powder by solubilizing pre-phenol powder in 0.448M sodium acetate buffer and extracting about four times with 0.448M sodium acetate, pH 6.9 buffered 72% phenol, followed by diafiltration to remove phenol from the aqueous phase, followed by recovery of the PRP as a precipitate by addition of CaCl$_2$ to about 0.05M and addition of ethanol to about 67%, followed by resolubilization in 0.05M CaCl$_2$ removal of contaminants insoluble in 20% ethanol, and recovery of post-phenol PRP as a 37% ethanol insoluble pellet and trituration in absolute ethanol; or PRP may be recovered from "Low-cut" by treatment with phospholipase, removal of protein and endotoxin as described above; or after production of endotoxin-free PRP by any appropriate means, preferably by treatment with HP20 resin as described above and in U.S. Pat. No. 5,019,502, 5,039,610, and U.S. Ser. No. 595,722.

Polysaccharide prepared according to the process of this invention is chemically indistinguishable by current analytical methods from polysaccharde produced by removal of endotoxin and lipid containing capsular polysaccharide by selective alcohol fractionation. In Table I below, the physico-chemical characteristics of PRP produced by PLD treatment are compared with the characteristics of PRP produced by selective alcohol fractionation:

TABLE I

|  | PLD TREATED PRP | ALCOHOL TREATED PRP |
| --- | --- | --- |
| % FA by GC | <0.012 wt % | <0.012 wt % |
| KD | 0.5 | 0.5 |
| ENDOTOXIN EU/μg | 0.01 Eu/mg | 0.6 Eu/mg |

Figure 3:
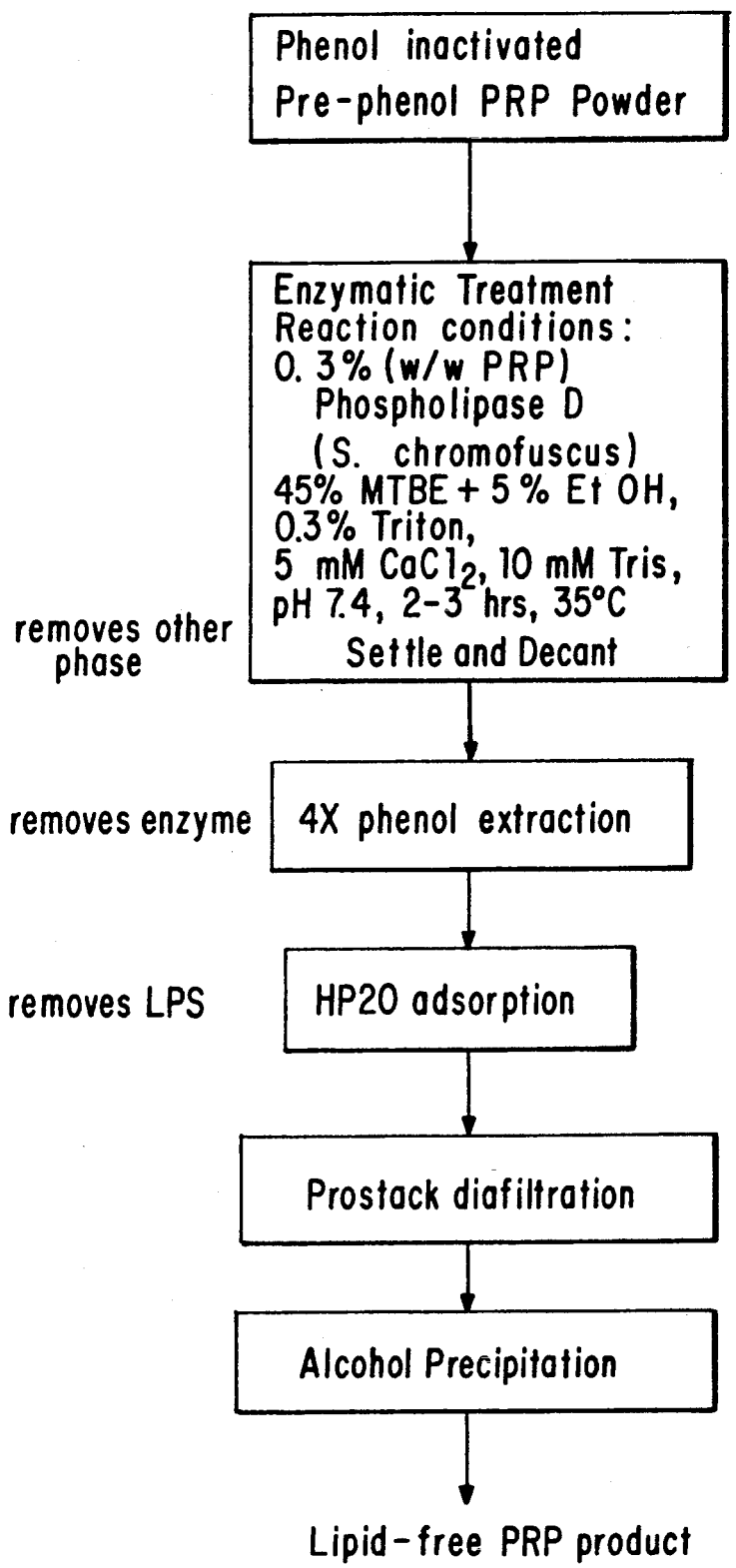
FIG. 3. Optimized process for conversion of lipo-PRP to lipo-free PRP and endotoxin removal.

A careful study to optimize each of the steps in the PRP production process was carried out. The results of these studies provided the scheme shown in FIG. 3.

A. Optimization of Enzyme Reaction Conditions:

A series of experiments was performed to map the sensitivity of the enzyme activity on lipid removal from low-cut powder as a function of methyl-tert-butyl ether content, amount of Triton, temperature, concentration of substrate, amount of enzyme, and reaction time in order to define acceptable limits on operating conditions. In each case the recommended condition is at or near the maximum level of fatty acid reduction.

B. Optimization of HP20 Treatment:

Studies were carried out to maintain better control of the pH during the HP20 LPS removal step in order to minimize potential hydrolysis of the PRP backbone. These studies included pre-equilibration of the resin with 2 volumes of DOC/sodium citrate solution, and following the pH drift during contact with a fresh buffer solution, as well as using a Tris-buffered DOC/sodium citrate solution and continuously monitoring the pH. Without pre-equilibration or buffering of the sodium citrate/DOC solution, the pH drifted as high to as 9.2–9.5 during a 3 hour batch adsorption. In the case of pre-equilibration, the upward pH drift was limited to 8.8. By pre-equilibrating the resin and also buffering the solution with 25 mM Tris, pH 8.0, the pH drift was even further minimized and a well-controlled pH of <8.5 could be maintained throughout the batch adsorption. Other conditions for the HP20 treatment of PRP were also examined. GC fatty acid analysis as well as LAL data suggested that optimal endotoxin removal was accomplished at 5–10 mg PRP/mL instead of the previously used 2.5 mg PRP/ml. The results also showed that a solution consisting of 0.5% DOC, 3% citrate and 50 mM Tris, pH 8.0 was superior. As a result, all subsequent HP20 treatments were carried out with resin pre-equilibration, using a 50 mM Tris, 0.5% DOC, 3% citrate, pH 8.0 solution at a PRP concentration of 5–10 mg/mL.

C. Evaluation of the Diafiltration Step:

After HP20 treatment the PRP product is in a solution containing Tris, DOC, and sodium citrate and the product needs to be exchanged into a neat aqueous solution via diafiltration. Two Pellicon units, one with a regenerated cellulose and the other with a polysulfone membrane were evaluated along with a polysulfone hollow fiber cartridge for diafiltration of the HP20-treated PRP solution. The regenerated cellulose membrane showed a greater DOC rejection rate than either of the polysulfone membranes; however, the Pellicon polysulfone membrane ex Hib ited significantly greater flux. The compelling flux and DOC rejection data suggested that a Prostack unit would be more effective than the currently employed hollow fiber membrane technology. By comparing the membrane area, process time, and cost requirements it was concluded that a Prostack unit with polysulfone membrane would provide the best performance.

From the foregoing studies, an enhanced PRP production process consisting of enzyme reaction, 4X phenol extraction, HP20 treatment, diafiltration, and alcohol precipitation was optimized and each of the steps was analyzed to define the operating limits. The enhanced process is summarized in FIG. 3.

The polysaccharide prepared according to this process is useful in the preparation of vaccines containing free or conjugated bacterial capsular polysaccharide. Conjugated polysaccharide, especially PRP-OMPC conjugates, are useful in infants to prevent disease, whereas the free PRP may not elicit sufficient immune responses. Preparation of conjugate using polysaccharide prepared according to this process may be accomplished by following the disclosure of U.S. Pat. No. 4,695,624 which is incorporated by reference, and the examples as provided herein.

The disclosure of this invention may be further comprehended with reference to the following examples which are not be considered as limiting the scope of the disclosure.

EXAMPLE 1

Preparation of *Haemophilus Influenzae* Type b Capsular Polysaccharide

Fermentation

A Stage: Inoculum and Seed Development

A lyophilized tube of *Haemophilus influenzae* type b, (cultured from Ross 768, received from State University of New York) was suspended in 1 ml of sterile Haemophilus inoculum medium (see below) and this suspension was spread on nineteen Chocolate Agar Plates (BBL). After 20 hours incubation at 37° C. in a candle jar, the growth on each plate was resuspended in 1–2 ml Haemophilus inoculum medium and pooled.

| Haemophilus Inoculum Medium* | |
|---|---|
| Soy Peptone | 10 gm/liter |
| NaCl | 5 gm/liter |
| $NaH_2PO_4$ | 3.1 gm/liter |
| $Na_2HPO_4$ | 13.7 gm/liter |
| $K_2HPO_4$ | 2.5 gm/liter |
| Distilled Water | To Volume |

*The pH of the solution is adjusted to a target value of 7.2 ± 0.1 (a typical value was pH 7.23) and the solution was sterilized by autoclaving at 121° C. for 25 minutes.

B Stage: 2-Liter Non-baffled Erlenmeyer Flasks

One-third portions of the resuspended bacteria from "A Stage" (above) were used to inoculate three two-liter flasks, each containing about 1.0 liter of complete Haemophilus seed and production medium (see below). The flasks were then incubated at 37° C. on a rotary shaker of 200 rpm for about 5 hours. A typical $OD_{660}$ value at the end of the incubation period was 0.37.

| Complete Haemophilus Seed & Production Medium | |
|---|---|
| $NaH_2PO_4$ | 3.1 g/l |
| $Na_2HPO_4$ | 13.7 g/l |
| Soy Peptone | 10.0 g/l |
| Yeast extract diafiltrate (1) | 10.0 ml/l |
| $K_2HPO_4$ | 2.5 g/l |
| NaCl | 5.0 g/l |
| Glucose (2) | 5.0 g/l |
| Nicotinamide adenine dinucleotide (NAD) (3) | 2.0 mg/l |
| Hemin (4) | 5.0 mg/l |

The salts and soy peptone were dissolved in small volumes of hot, pyrogen-free water and brought to correct final volume with additional hot, pyrogen-free water. The fermenters or flasks were then sterilized for about 25 minutes at 121° C. and after cooling, yeast extract diafiltrate (1), glucose (2), NAD (3), and hemin (4) were added aseptically to the flasks or fermenters prior to inoculation.

(1) Yeast extract diafiltrate: 100 g brewers' yeast extract (Amber) was dissolved in 1 liter distilled water and ultrafiltered in an Amicon DC-30 hollow fiber with H10X50 cartridges to remove molecules with m.w. 50,000. The filtrate was collected and passed through a 0.22 m membrane as a sterile product.

(2) Glucose was prepared as a sterile 25% solution in glass-distilled water.

(3) A stock solution of NAD containing 20 mg/ml was sterilized by filtration through a Millipore filter (0.22 m) and added aseptically just prior to inoculation.

(4) A stock solution of Hemin 3× was prepared by dissolving 200 mg in 10 ml of 0.1M NaOH and the volume adjusted with distilled, sterilized water to 100 ml. The solution was sterilized for 20 minutes at 121° C. and added aseptically to the final medium prior to inoculation.

C Stage: 70-Liter Seed Fermenter

Three liters of the product of "B Stage" was used to inoculate a 70-liter fermenter containing 41.4 liters of complete haemophilus seed and production medium (prepared as described above) and 17 ml UCON B625 antifoam. The pH started at 7.4.

The fermentation was maintained at 37° C. with 100 rpm agitation and monitored by optical density (O.D.) and pH determination until a typical O.D. of 0.39 was reached (after about 5.5 hours).

D Stage: 800-Liter Production Fermenter

Approximately 40 liters of the product of "C Stage" was used to inoculate an 800-liter fermenter containing 570 liters of production medium (prepared as described above), scaled to the necessary volume and 72 ml of UCON LB625 antifoam.

The fermentation was maintained at 37° C. with 100 rpm of agitation, with the O.D. and pH levels being checked about every two hours until the O.D. was similar for a two-hour period, at which time the fermentation was terminated (a typical final O.D. was 0.54 after 12 hours).

Harvest and Inactivation

Approximately 600 liters of the batch was inactivated by harvesting into a "kill tank" containing 12 liters of 1% thimerosal.

Clarification

After 8 hours inactivation at 4° C., the batch was centrifuged in 4-in. bowl Sharples centrifuges at a flow rate adjusted to maintain product clarity (variable between 1.3 and 3.0. liters/min). The supernatant obtained after centrifugation (15,000 rpm) was used for product recovery.

Isolation and Concentration by Ultrafiltration

The supernatant fluid from two production fermentations was pooled and concentrated at 2°–8° C. in a Romicon ultrafiltration unit with ten (50,000 Daltons cut-off) hollow fiber cartridges (275 $ft^2$ membrane area) such that after approximately 4.5 hours, 1200 liters had been concentrated to 32.5 liters. The filtrate was discarded.

48% and 61% Ethanol Precipitation

To the 32.5 liters of Romicon retentate, 30 liters of 95% ethanol was added dropwise over 1 hour with stirring at 4° C. to a final concentration of 48% ethanol by volume. The mixture was stirred two additional hours at 4° C. to ensure complete precipitation, and the supernatant fluid was collected through a single 4-inch Sharples centrifuge at 15,000 rpm (flow rate=0.27 liters/min). The insoluble pellet was discarded and the clarified fluid was brought to 61% ethanol with the addition of 20.8 liters of 95% ethanol over a one hour period. The mixture was stirred for three additional hours to insure complete precipitation.

Recovery of the Second Pellet

The resulting 48% ethanol soluble-61% ethanol insoluble precipitate was collected by centrifugation in the 4-inch Sharples centrifuge at 15,000 rpm (flow rate=0.62 liters/min.) and the 61% ethanol supernatant fluid was discarded. The crude product yield was 0.377 kg of wet paste, referred to as crude PRP.

Calcium Chloride Extraction

The 377 grams of 61% ethanol insoluble material, was mixed in a Daymax dispersion vessel at 2°-8° C. with 6.5 liters of cold, glass-distilled water. To this mixture, 6.5 liters of cold 2M $CaCl_2 \cdot H_2O$ was added, and the mixture (final concentration=1.0M $CaCl_2$) was extracted at 4° C. for 15 minutes. The vessel was then rinsed out with 2 liters of 1M $CaCl_2 \cdot H_2O$, resulting in 15 liters final volume.

23% Ethanol Precipitation

The 15 liters of $CaCl_2$ extract from above was brought to 23% ethanol by adding 4.48 liters of 95% ethanol dropwise, with stirring, at 4° C. over 30 minutes. After additional stirring for 17 hours, the mixture was centrifuged through a K2 Ultracentrifuge at 25,000 rpm (flow rate-165 ml/min) for 6.5 hours at 4° C. The supernatant fluid was decanted through cheese cloth to remove lipid-like floating material and the insoluble pellet was discarded.

37% Ethanol Precipitation and Collection of Crude Product Paste

The 23% ethanol-soluble supernatant fluid was brought to 37% ethanol by the addition of 4.33 liters of 95% ethanol, dropwise with stirring, over a 30 minute period. The mixture was then allowed to stand with agitation for one hour, then without agitation for 14 hours, to ensure complete precipitation. The resulting mixture was then centrifuged in a 4-inch Sharples unit at 15,000 rpm (flow rate=0.2 liters/min) to collect the pelleted crude polysaccharide (referred to hereinafter as pre-phenol powder).

Trituration

The pellet from the centrifugation was transferred to a 1-gallon Waring Blender containing 1 liter of absolute alcohol and blended for 30 seconds at the highest speed. Blending was continued at 30 seconds on and 30 seconds off until a hard, white powder resulted. The powder was collected on a Buchner funnel with a teflon filter disc and washed sequentially in situ with two 1-liter portions of absolute ethanol and two 2-liter portions of acetone. The material was then dried in vacuo, at 4° C., for 24 hours, resulting in 68 g (dry weight) of product.

Phenol Extraction

The 68 grams of dry material from the trituration step was resuspended in 12 liters of 0.488M sodium acetate, pH 6.9, with the aid of a Daymax dispersion vessel. The sodium acetate solution was immediately extracted with 4.48 liters of a fresh aqueous phenol solution made as follows: 900 ml of 0.488M sodium acetate, pH 6.9, was added to a five-pound bottle of phenol (Mallinckrodt crystalline) in a 20-liter pressure vessel and mixed until a complete solution was effected. Each phenol extract was centrifuged for 2½ hours at 30,000 rpm and 4° C. in the K2 Ultracentrifuge (Electronucleonics) in order to break the emulsion. The aqueous effluent was extracted three additional times with 3.2 fresh aqueous phenol solution in a similar manner. The phenol phases were discarded.

Diafiltration

The aqueous phase from the phenol extractions above (17.6 liters) was diluted with 300 liters of cold, glass-distilled water and diafiltered at 4° C. on an Amicon DC-30 ultrafiltration apparatus using 3 H10P10 cartridges. The Amicon unit was rinsed and the rinse added to the retentate, such that the final volume was 17.5 liters. The ultrafiltrate was discarded.

67% Ethanol Precipitation 0.438 liters of 2.0M $CaCl_2$ was added to the 17.5 liters of dialysate from the previous step (final $CaCl_2$ concentration was 0.05M) and the solution was made 67% ethanol with dropwise addition over one hour of 35.88 liters of 95% ethanol to the rapidly-stirring solution. After 4 hours of agitation, then standing for 12 hours more at 4° C., the clear supernatant fluid was siphoned off and the precipitate was collected by centrifugation in the 4-inch Sharples centrifuge (15,000 rpm), at 4° C. for 45 minutes. The resulting polysaccharide pellet was triturated in a 1-gallon Waring blender using the 30 seconds on 30 seconds off method with 2 liters of absolute ethanol, collected on a Buchner funnel fitted with a teflon filter disc, and washed in situ with four 1-liter portions of absolute ethanol followed by two 1-liter portions of acetone. The sample was then dried in a tared dish in vacuo at 4° C. for 20 hours. The yield was 39 grams of dry powder (referred to as post-phenol powder).

EXAMPLE 2

Preparation of Crude PRP from Phenol Killed *Haemophilus influenzae* type b

The same fermentation procedure of Example 1 is followed except that in place of 1% thimerosal inactivation, the pathogen is killed by addition of 0.5% phenol, and incubation of the cells in phenol for 1 hour, followed by transfer to a kill tank for a minimum of one hour. The same procedure was then followed as per Example 1 to provide pre-phenol powder.

EXAMPLE 3

Preparation of "Low-Cut" and Retrieval of Lipid-Free PRP Therefrom

Following production of post-phenol powder, according to Example 1, residual endotoxin was removed by selective alcohol fractionation to provide an endotoxin-free PRP preparation, and an endotoxin containing PRP fraction called low-cut. This was accomplished by solubilizing post phenol powder at 2.5 g/L in 0.05M CaCl$_2$ to provide a divalent counter ion for both endotoxin and PRP. Alcohol was then added to 26% (v/v). After the temperature equilibrated to a constant value in the 2° to 4° C. range, alcohol was added incrementally until the PRP began to precipitate (cloud point), causing turbidity as monitored by a turbidity probe.

Ethanol (95%) was added to the cloud point, and then an additional 1.9% was added. The precipitate is termed "low-cut". After the alcohol was added, the solution was immediately centrifuged to remove low-cut precipitate, from which lip-PRP was further processed according to the process of this invention to yield lipid-free PRP as described further below. Additional alcohol was added to the supernatant to 38% (v/v). The desired precipitate was collected via settling and/or centrifugation and dried to the final powder. Typical recoveries for this step at 1.2-2.0% above the cloud point were 25-40% of the post-phenol powder. The remainder of the PRP is found in the low-cut.

The low-cut material obtained after performing the selective ethanol fractionation step, containing precipitated lipopolysaccharide and polyribosylribitol phosphate, was further treated by reacting a 20 g/L solution of low-cut in 750 mL buffer (10 mM Tris, 5 mM CaCl$_2$, 4.5 mM Triton X-100, pH 7.4 and an equal volume of a 9:1 mixture of methyl tert butyl ether:ethanol), and adding 3000 U phospholipase D. The reaction was allowed to proceed for 2.5 hours, following which the material was phenol extracted four times using 1 part phenol (72% solution in sodium acetate) per 2.6 parts of aqueous product.

Endotoxin was removed from the PLD treated low-cut by mixing with 0.5% sodium deoxycholate and 3% sodium citrate at pH 8. HP20 resin was added at 30 grams resin per gram polysaccharide (the resin was washed prior to use with pyrogen free water). The loose beads were mixed with the solution on an orbital shaker for 3 hours at 4° C. After mixing, the beads were removed from the solution in a stainless steel filter funnel. The filtrate was then diafiltered in a Pellicon polysulfone 10,000 molecular weight cutoff membrane (1 ft$^2$ surface area) vs. 10 vol. of pyrogen free water, maintaining an estimated polysaccharide concentration of ≤2.5 mg/ml, to remove detergent and chelating agent. The retentate was recovered and 2M calcium chloride was added to achieve a final calcium chloride concentration of 0.05M. Polysaccharide was precipitated from solution with excess 95% ethanol. The precipitate was centrifuged at 13,000×g for 30 minutes, the pellet triturated with absolute ethanol and acetone, and then vacuum dried. The final powder was transferred to a sample container and frozen at −70° C.

Material treated with resin showed the following reductions of endotoxin levels, polysaccharide levels, and levels of lipo-PRP (Fatty acid by GC):

TABLE 2

| LAL test value EU/mcg | |
| --- | --- |
| initial | 240 |
| final powder | 0.12 |
| Polysaccharide | |
| initial | 15 g |
| final powder | 10.2 g |
| Fatty Acid (%) | |
| initial | 0.4 |

TABLE 2-continued

| final powder | 0.009 |
| --- | --- |

This process consistently yields a product recovery ratio of about 68%, which is the ratio of weight of final product to starting material, and it is indistinguishable in its physico-chemical properties from the PRP product obtained by selective alcohol fractionation.

EXAMPLE 4

DELIPIDATION OF PRE-PHENOL PRP POWDER

A. Phospholipase D Reaction:

Pre-phenol PRP powder (20 grams, prepared according to Example 2 or Example 3) was solubilized in 1.33 liters of 10 mM Tris, 5 mM CaCl$_2$, 4.5 mM Triton X-100, pH 7.4. To the solubilized PRP was added 1.33 liters of a 9:1 mixture of methyl tert butyl ether:ethanol. Phospholipase D (Genencor, 3000 units total, specific activity 70 u/mg, 15 units/100 mg PRP) was added. The reaction was stirred at 240 rpm and allowed to proceed for 3 hours at 35° C.

Following the reaction, the organic and aqueous phases were allowed to separate for 30 minutes at 25°-35° C., and the lower aqueous phase was retained. The organic phase was re-extracted with 0.266 liters of water which was allowed to settle for 30 minutes and then combined with the first extraction to yield a total aqueous volume of 1.560 liters.

Phenol (1.5 kilograms equilibrated with 590 mL of 0.448M Sodium Acetate, pH 6.9) was dissolved in the dark. The aqueous phase was extracted four times using 1 part phenol per 2.6 parts aqueous product post phenol sample.

B. HP20 Treatment:

HP20 (Mitsubishi Kasei, 300 grams) was pre-equilibrated in 1300 mL of 50 mM Tris, 0.5% DOC, 3% Sodium Citrate, pH 8.0 (HP20 equilibration buffer). To 1060 mL of the post phenol sample, 1060 mL of 100 mM Tris, 1% DOC, 6% Sodium Citrate, pH 8.0 was added to yield a total volume of 2120 mL. This sample was then mixed for 2 hours at 4° C. with shaking with the pre-equilibrated HP20 resin. The resin was filtered off into a column which was then rinsed with 200 mL HP20 equilibration buffer. The total HP20 flow through was then concentrated to 1 liter, and diafiltered against 10 liters of cold, pyrogen-free water.

C. Product Recovery:

To the 1 liter sample, 25 mL of 2M CaCl$_2$, was added. The precipitate was collected by centrifugation for 30 minutes at 4° C., and the pellet was then triturated with 20 mL 100% ethanol. The ethanol was filtered off and the PRP powder was dried with acetone, to yield a total of 9.6 grams of delipidated PRP with the following characteristics:

TABLE 3

| | LAL (Eu/µg) | PRP | Fatty Acid |
| --- | --- | --- | --- |
| initial | 2400 | 20 g | 1.9% |
| final | 0.48 | 9.6 g | 0.005% |

EXAMPLE 5

Production of Phospholipase $A_2$ and Phospholipase D Treated PRP, Conjugation with OMPC of Neisseria Meningitidis B. and Immunogenicity of the Conjugate

A. Enzymatic Treatment:

HP20 treated post-phenol powder (3 g) was solubilized in 600 mL phosphate buffer, pH 7.1, 0.1% deoxycholate, 33% ether, at a concentration of 5 mg/mL PRP. Phospholipase $A_2$ (porcine, 70 u/mg PRP, specific activity 600 u/mg) and phospholipase D (Streptomyces chromofuscus, 0.2 u/mg PRP, specific activity 70 u/mg) (both from Boehringer Mannheim, Inc.) were added and the reaction allowed to proceed at 25° C. for 3 hours with agitation. The reaction products were extracted with 600 mL hexane, followed by centrifugation for 30 minutes at 20° C. The organic phase was discarded, while the aqueous phase was concentrated to 300 mL and diafiltered against 3000 mL water. The sample was diluted to 600 mL and a final concentration of 5 mM $CaCl_2$, and the PRP was precipitated by addition of ethanol to 40%, yielding 2.6 g PRP for conjugation.

B. Derivatization of the $PLA_2$/PLD Treated PRP:

Post-HP20 PRP (1.9 g) treated as described above with PLA2 and PLD was solubilized in 57 ml sterile water. Oxalic acid dihydrate (0.31 g) was dissolved in 15.5 ml sterile water and the solubilized PRP was added slowly. The pH was adjusted to pH 5 with 40% tetra-n-butylammonium hydroxide (5 ml) followed by addition of 1% tetra-n-butylammonium hydroxide (2 ml) and the pH titrated to 6.98 with oxalic acid solution. The solution was then filtered and the filter rinsed, yielding a total prep. volume of 178 ml of PRP-Bu4N.

To this solution was added 67 ml of DMF and the volume reduced to 68 ml on a rotory evaporator. Additional DMF (67 ml) was added 3 times, each time bringing the volume to 67 ml: carbonyl diimidazole (0.22 g) was dissolved in DMF and added slowly to the PRP solution under an atmosphere of $N_2$ and allowed to age for 35 min. 1,4-butanediamine dihydrochloride ($BuA_2$) (15.96) was dissolved in 456 ml sterile water, and the pH was adjusted to 10.39 by addition of 5 ml of 50% NaOH. The BuA2 was then slowly added to the PRP-CDZ and maintained at about 12° C.

After about 5 minutes, 68% phosphoric acid (50 ml) was added, and the pH adjusted to 7.02 by dropwise addition of 5 ml 68% phosphoric acid. The volume at this point was 530 ml.

The sample was concentrated to 95 ml on an Amicon ultrafiltration system using a 10,000 MW cutoff. The sample was then diafiltered against 1520 ml phosphate buffer pH 7. The ultrafiltration system was washed with 3×25 ml aliquots of phosphate buffer which were combined with the PRP-BuA2 retentate, to yield a total volume of 102 ml sodium borate (3.95%, 31.8 ml) was then added to the PRP-BuA2.

The pH was adjusted to 9.2 with 2 ml of 2.5N NaOH. Bromoacetyl chloride (1.71 ml) was then added slowly while the pH was maintained at 9.2 using 2.5N NaoH. The pH was then adjusted to 7.0 with 68% phosphoric acid (0.5 ml). The PRP-BuA2-BrAc was concentrated to 95 ml on an Amicon ultrafiltration system, followed by diafiltration against 1520 ml pH 7 phosphate buffer, and the volume adjusted to 38 ml by diafiltration. The system was washed with phosphate buffer, and the washes combined to yield 79.5 ml of PRP-BuAz-BrAc.

C. Preparation of OMPC-SH:

OMPC from Neisseria meningitidis type b (1.16 g) was solubilized in 116 ml sterile water and then diafiltered against 600 ml of borate buffer, to yield a final volume of 159 ml. EDTA (0.8 g), Dithiothreitol (DTT) (0.12 g) was dissolved in sterile borate buffer and then added to the solubilized protein. N-acetylhomocysteine thiolactone (1.03 g) was dissolved in sterile water, and then added to the protein, EDTA, DTT mixture and allowed to react for 22 hours.

The thiolated protein was then concentrated to 116 ml and then diafiltered against 1440 ml of pH 8 phosphate buffer, followed by concentration to 127 ml final volume. A protein assay at this point revealed 6.75 mg/ml protein, and on Ellman assay revealed 0.3 $\mu$moles SH per milligram of protein.

D. Conjugation of Derivatized PRP and OMPC-SH:

The pH of the PRP-BuA2-BrAc solution was adjusted to 7.9 with 2.5N NaOH. To 72 ml of the pH ed PRP-BuA2-BrAc was added all of the thiolated OMPC prepared in subsection B above, and conjugation was allowed to proceed for 19 hours under an atmosphere of $N_2$.

The conjugate was concentrated to 170 ml followed by diafiltration against 1700 ml of pH7 phosphate buffer, followed by diafiltration against 1640 ml of pH8 phosphate buffer, yielding a final volume of 231 ml of conjugate.

Unreacted bromocetyl groups on the conjugate were capped by adding N-acetylcysteamine (0.95 g in pH8 phosphate buffer) and the reaction allowed to proceed for 18 hours. The capped conjugate was then concentrated to 170 ml, and diafiltered against 2550 ml of TED buffer. The conjugate was allowed to age overnight and was diafiltered against a second 2550 ml of TED buffer. A final sample volume of 285 ml was recovered.

In a parallel experiment, 2.31 g of PRP produced by selective alcohol fractionation was conjugatedas described above, to yield 330 ml of conjugate. Side by side analysis of the physico-chemical properties of the two conjugates were indistinguishable by size exclusion chromatographic, pyroge, PRP/protein, or immunogenicty analyses.

E. Immunogenicity of the Conjugate in Infant Rhesus Monkeys:

The enzyme treated lipid-free PRP conjugate vaccine has been shown to be fully immunogenic in infant rhesus monkey tests conducted according to the assay of Vella and Ellis [Pediatric Res. 29, 10 (1981)], and Vella, et al. [Pediatrics Supplement, 85, 668 (1990)]. The lipid-free conjugate showed comparable immunogenicity to the control samples made with PRP prepared by selective alcohol fractionation. After 42 days in both aqueous (15 mcg) and aluminum hydroxide (1 mcg) formulations (Tables 4 and 5). As shown in Table 5, aqueous enzyme-treated lipid-free vaccine produced a GMT (geometric mean titre) for three animals of 10.9 mcg/mL.

TABLE 4

IMMUNOGENICITY OF "LIPID-FREE" Hib CONJUGATES IN INFANT RHESUS MONKEYS LIQUID ALUMINUM HYDROXIDE ADSORBED FORMULATION

| Hib Conjugate | Dose mcg | Anti-PRP, mcg/mL (GMT) | | |
|---|---|---|---|---|
| | | day 0 | 28 | 42 |
| enzyme-treated lipid free PRP | 1 | <0.1 | 27.4 (3/3) | 79.1 (3/3) |
| PRP from selective | 1 | <0.1 | 10.9 (3/3) | 74.0 (3/3) |

TABLE 4-continued
IMMUNOGENICITY OF "LIPID-FREE" Hib
CONJUGATES IN INFANT RHESUS MONKEYS LIQUID
ALUMINUM HYDROXIDE ADSORBED FORMULATION

| Hib Conjugate | Dose mcg | Anti-PRP, mcg/mL (GMT) | | |
|---|---|---|---|---|
| | | day 0 | 28 | 42 |
| alcohol fractionation | | | | |

TABLE 5
IMMUNOGENICITY OF "LIPID-FREE" Hib
CONJUGATES AND "HP20-TREATED" CONJUGATE
IN INFANT RHESUS MONKEYS
AQUEOUS FORMULATION

| Hib Conjugate | Dose mcg | Anti-PRP, mcg/mL (GMT) | | |
|---|---|---|---|---|
| | | day 0 | 28 | 42 |
| enzyme-treated lipid free PRP | 15 | <0.1 | 0.4 (0/3) | 10.9 (3/3) |
| selective alcohol fractionated PRP | 15 | <0.1 | 0.9 (1/3) | 6.5 (2/3) |

( )Number of responders achieving ≧1.0 mcg anti-PRP/mL (RIA)

EXAMPLE 6
Retrieval of Lipid-Free PRP from "Low-Cut"

Low cut (15 g) was solubilized in 750 mL buffer (10 mM Tris, 5 mM $CaCl_2$, 4.5 mM Triton X-100, pH 7.4). Phospholipase D (20U Toyo Joso/100 mg PRP, 3000 units at 70 U/mg) was added. A mixture of methyl tert-butyl ether:ethanol (9:1) (750 mL) was added and agitation provided at 240 rpm. The reaction was allowed to proceed for 2.5 hours at 35° C. An additinal 2964 units of PLD was added, then the reaction was allowed to separate into phases for 20 minutes at room temperature. The aqueous PRP phase was retained. The organic phase was extracted with 150 mL water and the 156 mL or lower phase was added to the first aqueous phase.

The 950 mL of aqueous PRP was extracted four times with phenol equilibrated with sodium acetate at a ratio of phenol:water=1:2.6.

The phenol extracted PRP was then treated with 450 grams of citrate/DOC (0.5% DOC, 3% Sodium Citrate, 5 mM Tris, pH 8.0) pre-equilibrated HP20 resin for 2 hours at room temperature. The beads were filtered and the aqueous phase retained. A 292 mL buffer was of the beads was combined with the bulk of the aqueous phase, which was then diafiltered (Pellicon 1 $ft^2$, 10,000 mw cutoff membrane). The PRP was then concentrated to 1 L and precipitated by addition of ethanol to 40%. The precipitate was collected by centrifugation, triturated in 95% ethanol, and dried in acetone.

The PRP obtained in this example was found to be comparable to selective ethanol fractionated PRP by all parameters tested.

EXAMPLE 7
Phenol-Inactivation of *Haemophilus influenzae* Type b

The *H. influenzae* culture containing approximately $10^9$ organisms per mL is inactivated at the end of the fermentation cycle by adding phenol to the fermentation culture to approximately 0.5% (w/v) final concentration, transferring the culture after verification of the phenol concentration to an agitated "kill" tank, and exposing the culture to phenol for a minimum period of one hour at 37° C. Although laboratory experiments described below demonstrate that an 8 log inactivation of the culture is achieved after a period of seven minutes in the presence of 0.5% phenol, the inactivation period at production scale was extended to one hour to achieve a higher level of safety.

Culture inactivation study (laboratory scale)

*H. influenzae* culture was cultivated in a 37° C. shaker incubator to stationary phase. Aliquots of the resulting culture containing approximately $10^9$ cells per mL were exposed to 0.2, 0.3, 0.4, 0.5 and 0.6% (w/v) phenol 37° C. Phenol concentrations of 0.2% and 0.3% had little effect on inactivating the culture within the 10-minute exposure period. However, a significant rate of inactivation was obtained at 0.4 and 0.5% phenol. After 7 minutes at 0.5% phenol, there were no viable cells detected in a plating assay with demonstrated sensitivity to a limit of approximately 10 CFU/mL in the presence of phenol. The inactivation kinetics at both 0.4 and 0.5% phenol concentration were found to be biphasic. At 0.6% phenol, the inactivation was so rapid that no viable cells were detected after 30 seconds of phenol exposure.

Production scale inactivation studies

The reactor containing approximately $10^9$ organisms per mL was brought to approximately 0.5% phenol and the CFU/mL was determined as a function of exposure time. Due to the mechanics of sampling, only two measurements a minute apart could be made. For the reactor which had a six minute mixing time for full distribution of phenol, a 7 log reduction was observed during the first three minutes. After five minutes, no viable cells were detected in a plating assay with demonstrated sensitivity to a limit of approximately 10 CFU/mL in the presence of phenol.

EXAMPLE 8
Clearance of Phospholipase D

The Enhanced PRP Process was designed to effectively eliminate PLD from the final PRP powder. The amount of residual enzyme remaining in the PRP was estimated by a number of approaches described below. These approaches included direct assay for PLD and for enzyme activity in final PRP preparations, analysis for PLD in in-process samples, and PLD spike-recovery studies at each step of the process. Additionally, attempts were made to raise antibodies to PLD for use in immunological assays. Each of these approaches is described below.

Direct Assay of PLD in final PRP powders

Direct assay of PLD in the final PRP powders by SDS-PAGE with Coomassie staining (the PLD preparation does not stain well with silver) showed that the residual level of PLD was less than the limit of detection (<250 ng PLD/lane). By maximizing the load on the gel, the residual PLD level corresponded to <5 ng/mg PRP or <0.0005%. This limit of detection is equivalent to <1 ng/dose.

The final PRP powders were also assayed for residual PLD enzymatic activity and no activity was detected. The detection limit of the enzymatic assay was 6 ng PLD/mL ($6 \times 10^{-4}$ U PLD/mL) which corresponded to <64 pg active PLD/mg PRP. Additional studies were carried out which showed that exposure of PLD to phenol inactivated the enzyme.

Direct analysis for PLD in in-process samples

In-process manufacturing samples were assayed directly for residual PLD by SDS-PAGE with Coomassie staining. The level of PLD in PRP after the first phenol extraction was below the detection limit, which corresponded to a PLD level of <5 ng PLD/mg PRP. This showed by direct measurement that the first phenol extraction reduced the PLD level by almost 3 logs (from ~2.4 mcg PLD/mg PRP in the reaction mixture to less than 5 ng PLD/mg PRP in the first phenol extract). Further processing by three additional phenol extractions, HP20 treatment and alcohol precipitation provided additional PLD clearance, although the levels were too low to be determined directly.

PLD Spike and Recovery Studies

Because the residual PLD level in in-process samples was too low to measure directly, an extensive series of PLD spike-recovery studies were carried out in the laboratory to estimate the amount of PLD that could be removed per isolation step. Three different isolation steps were identified as effective in removing enzyme First, the effectiveness of the phenol-extractions for removing PLD was studied. A concentrated solution of PLD at 8 mg/mL in 20 mg PRP/mL was subjected to 4 phenol-extractions, and each of the aqueous layers was monitored for PLD by SDS-PAGE. After a single phenol-extraction, the level of PLD was below the limit of detection of 250 ng PLD/lane by SDS-PAGE with Coomassie staining which represented a reduction of 800-fold or almost 3 logs clearance. In another experiment, a batch of PLD was fluorescently labelled with fluorescein-5-isothio-cyanate (FITC). Using the FITC-tagged PLD, the partition coefficient of the enzyme as a function of its concentration in phenol was measured by fluorescense spectroscopy. This technique provided an additional 10-fold increase in sensitivity in the PLD detection level. This method again confirmed that a single phenol extraction was effective in reducing the enzyme level by at least 2 logs.

To determine the effect of HP20 treatment on PLD removal, an adsorption isotherm of PLD in 5 mg PRP/mL on HP20 resin was measured. The steep slope of the isotherm indicates that the resin has a strong affinity for PLD which translates into a least 2 logs of clearance for PLD under the specific conditions of the HP20 treatment. The residual enzyme at this step, which is subsequent to four phenol-extractions, would already be very low, but these data show that any residual enzyme would be further eliminated by selective adsorption to the HP20 resin.

Finally, in small-scale spiking experiments, 90% of the enzyme remained in the supernatant upon alcohol-precipitation. Thus, this final step provides the potential for an additional 10-fold clearance.

These studies demonstrated that the bulk of the enzyme (>99.99%) is removed by the four phenol-extractions. Since the distribution coefficient of the enzyme between water and the phenol phase in the presence of PRP was determined to be $10^2$, four phenol extractions could in theory provide $10^8$-fold clearance; however, an estimate of $10^3$-fold clearance was conservatively assigned to this step. Based on the adsorption isotherm measurements, $10^2$-fold clearance was estimated for the HP20 adsorption. A 10-fold PLD reduction was attributed to the alcohol fractionation step. In all, a conservative estimate of $10^6$-fold total enzyme clearance was assigned to the Enhanced PRP Process. Actual clearance could theoretically be as high as $10^{11}$-fold.

The table below summarizes the findings from these clearance studies. The last column provides a calculation of the remaining PLD/dose for each method of determination. Note that all calculations were based on the premise that 300 mcg of PRP goes into the conjugation reaction to yield a 15 mcg dose. This provides a conservative approach for estimating the amount of residual enzyme per dose.

| Estimate of Enzyme Clearance Based on Several Methods of Determination | | |
|---|---|---|
| Method of Determination | Enzyme Clearance | PLD/Dose Vaccine (NG) |
| No clearance of PLD | 0 | $10^3$ |
| LOD* for direct measurement | 3 logs | <1 |
| Estimated clearance, conservative | 6 logs | $<10^{-3}$ |
| Calculated theoretical clearance | 11 logs | $<10^{-8}$ |

*Limit of detection

EXAMPLE 9

Comparative Analysis of Enhanced- and Alcohol Fractionation Process PRP

All lots of PRP manufactured by the Enhanced Process were subjected to extensive analytical testing to determine their chemical and physical comparability to PRP preparations made by the selective alcohol fractionation process. The results of these analyses are described below.

A. NMR Analysis

Proton-NMR analysis of the three manufacturing consistency lots of PRP prepared by the Enhanced PRP Process and one representative lot made by the selective alcohol fractionation process showed that these samples were essentially equivalent. The spectra for these samples showed indentical spectra in the region from $\delta H = 3.72$ to 5.2.

B. Carbohydrate Composition Analysis

The compositional integrity of PRP samples was assessed by determining the identity and the relative amounts of the component saccharides in the PRP preparations. This was accomplished by acid hydrolysis of the PRP samples and subsequent quantitation of the carbohydrate components (ribitol and ribose) by high pH anion exchange chromatography with pulsed amperometric detection. Three Enhanced Process PRP demonstration lots and two representative selective alcohol fractionation process PRP lots were analyzed. Comparative analysis of these samples based on peak area ratios of ribitol-to-ribose showed that the five lots are essentially identical. Additionally, the trace component peaks were comparable in all five preparations. The level of these components was less that 1 mole % relative to ribitol or ribose.

C. Fatty Acid Analysis

Comparative fatty acid analysis of selective alcohol fractionation production PRP and Enhanced Process PRP products was undertaken. The former production process PRP samples contain varying small amounts of fatty acids, while Enhanced Process PRP samples contain ≦0.002% (w/w) fatty acid by capillary gas chromatographic analysis of the fatty acid methyl esters.

D. Molecular Size Analysis

Sepharose 4B analysis

The molecular size of PRP preparations is currently determined by Sepharose 4B column chromatography with refractive index detection, which provides a measure of the relative molecular size of the PRP preparation in terms of a relative elution volume ($K_d$). $K_d$'s for representative samples are shown below. Based on these analyses there are no apparent differences in molecular sizes among the five PRP preparations.

| Measurement of molecular size based on Sepharose 4B analysis | |
|---|---|
| Sample | $K_d$ |
| Enhanced PRP: | |
| Sample 1 | 0.46 |
| Sample 2 | 0.48 |
| Sample 3 | 0.45 |
| Selective Alcohol Fractionation PRP: | |
| Sample 1 | 0.46 |
| Sample 2 | 0.51 |

HPSEC-universal calibration analysis

In addition to the Sepharose 4B analysis, the molecular size and polydispersity of each of the above PRP preparations were examined by high performance size exclusion chromatography with on-line specific viscosity and refractive index detection. This analysis is done using a TSK G4000 PWXL column in an ammonium acetate mobile phase, and allows the calculation of a relative molecular weight ($M_p$) and polydispersity index (PI) for each PRP preparation. Chromatograms resulting from analysis of the three demonstration lots of Enhanced Process PRP and two representative lots of selective alcohol fractionation process PRP are summarized below. The average results from analysis of a total of 29 selective alcohol fractionation production PRP lots are also shown in the table.

| Determination of relative molecular weight ($M_p$) and polydispersity index (PI) of PRPs prepared by the Enhanced and selective alcohol fractionation processes | | |
|---|---|---|
| Sample | $M_p$ | PI |
| Enhanced PRP | | |
| Sample 1 | 202,000 | 1.80 |
| Sample 2 | 183,000 | 1.65 |
| Sample 3 | 213,000 | 1.56 |
| Average of 3 lots | 199,000 ± 15,000 | 1.67 ± 0.12 |
| Selective Alcohol Fractionation PRP | | |
| Sample 1 | 165,000 | 1.54 |
| Sample 2 | 148,000 | 1.42 |
| Average of 29 lots | 150,000 ± 21,000 | 1.39 ± 0.12 |

Results of these analyses provide reasonable evidence that PRP preparations made by the Enhanced Process are slightly larger and more polydisperse than PRP preparations manufactured by the selective alcohol fractionation process.

In addition to the above analyses, the derivatized PRP corresponding to each of the above Enhanced Process PRP preparations, and representative samples of derivatized selective alcohol fractionation process PRP were analyzed for molecular size. The molecular size and polydispersity of the derivatized PRP preparations (bromoacetyl butanediamine form) were examined by both Sepharose 4B chromatography and by HPSEC-universal calibration. The results of those analyses are shown below.

| Measurement of molecular size and polydispersity of Enhanced- and selective alcohol fractionation process derivatized PRPs | | | |
|---|---|---|---|
| Sample | $K_d$ | $M_p$ | PI |
| Derivatized Enhanced PRP | | | |
| Sample a | 0.64 | 105,000 | 1.37 |
| Sample b | 0.61 | 123,000 | 1.48 |
| Sample c | 0.60 | 127,000 | 1.42 |
| Average | 0.62 | 118,000 + 12,000 | 1.43 ± 0.06 |
| Derivatized Selective Alcohol Fractionation PRP | | | |
| Sample a | 0.65 | 104,000 | 1.32 |
| Sample b | 0.59 | 112,000 | 1.29 |
| Sample c | 0.60 | 119,000 | 1.33 |
| Average | 0.61 | 112,000 ± 8,000 | 1.31 ± 0.02 |

These results indicate that PRP is reduced in size during derivatization and that the resulting molecular sizes of the derivatized Enhanced Process PRP and the derivatized selective alcohol fractionation process PRP are essentially equivalent.

E. Relative Antigenicity Analysis

The PRP antigen content is typically determined by rate nephelometry analysis. Comparison of the antigen concentration of a given sample with the polysaccharide concentration gives a measure of the relative antigenicity of the sample. Results of such analyses for three demonstration lots of Enhanced Process PRP and for two representative selective alcohol fractionation process PRP lots are provided below. For these five samples, the relative antigenicities are equivalent within experimental error.

| Comparison of the Relative Antigenicity of Enhanced- and Selective Alcohol Fractionation Process PRPs | |
|---|---|
| Sample | Relative Antigenicity (%) |
| Enhanced Process PRP | |
| Sample 1 | 93 |
| Sample 2 | 95 |
| Sample 3 | 101 |
| Selective Alcohol Fractionation PRP | |
| Sample 1 | 96 |
| Sample 2 | 105 |

EXAMPLE 10

Animal Immunogenicity Test Results

A. Immunogenicity in Infant Rhesus Monkeys

Infant Rhesus monkeys have been used as a preclinical immunogenicity model which correlates with the immunogenicity of *H. Influenzae* conjugate vaccines in human infants. Haemophilus b Conjugate Vaccine (Meningococcal Protein Conjugate) has been tested extensively in this species and found to be highly immunogenic (Vella et al., *Pediatrics*, 85, 668, 1990; Vella and Ellis, *Pediatric Research* 29, 10, 1991). Only a small number of monkeys are available for use each year, such that we use 3-6 monkeys/group to test each vaccine. Being an outbred species, we have found a variation of up to ca. 100-fold in anti-PRP levels across individual infant monkeys in response to Haemophilus b Conjugate Vaccine (Meningococcal Protein Conjugate), similar to the degree of variation in the immune response of individual human infants. For these reasons of group size and outbred nature, the infant Rhesus monkey is a qualitative rather than quantitative model for the immunogenicity of these vaccines. We consider a positive response to be post-dose 2 level of >1 mcg anti-PRP/mL, a level not achieved by PRP, PRP-D or HbOC vaccines. We consistently achieve this level with Haemophilus b Conjugate Vaccine (Meningococcal Protein Conjugate).

Anti-PRP responses of infant Rhesus monkeys to Haemophilus b Conjugate Vaccine (Meningococcal Protein Conjugate) prepared with PRP from the Enhanced PRP Process are comparable to the original Research and Manufacturing consistency lots and to a production lot prepared by the selective alcohol fractionation process. Included in the testing was a Research-prepared conjugate using PRP made in the laboratory with the Enhanced Process, and four conjugate lots made from three lots of Enhanced PRP. In all, a tototal of 24 monkeys have been immunized with Haemophilus b Conjugate Vaccine (Meningococcal Protein Conjugate) prepared with PRP from the Enhanced PRP Process. All 24 monkeys achieved post-dose 2 levels of >1 mcg anti-PRP/mL. These data demonstrate the immunological equivalence of Haemophilus b Conjugate Vaccine (Meningococcal Protein Conjugate) prepared with PRP from the Enhanced Process and by the selective alcohol fractionation process in this qualitative model of immunogenicity.

B. Mouse Immunogenicity Data

Potency testing of the Haemophilus b Conjugate Vaccine (Meningococcal Protein Conjugate) prepared with PRP from the Enhanced Process has also been performed in BALB/c mice. Being a genetically inbred species and available in essentially unlimited number, potency testing in these mice is a quantitative model for immunogenicity of this vaccine. In this model, serial 5-fold dilutions of vaccine are injected into each group of 8 mice, for a total of 40 mice for each vaccine lot. The effective dose for seroconverting 50% of the mice ($ED_{50}$) to seropositivity for anti-PRP is calculated for each set of 40 mice (the lower the $ED_{50}$, the higher the potency). The $ED_{50}$ values for 4 different lots of Haemophilus b Conjugate Vaccine (Meningococcal Protein Conjugate) prepared with PRP from the Enhanced PRP Process are in the same range as the Haemophilus b Conjugate Vaccine (Meningococcal Protein Conjugate) reference control which has been shown to be immunogenic in human infants. These data demonstrate immunological comparability in a quantitative model.

EXAMPLE 11

Test results for the *H. influenzae* fermentation lots used in the Enhanced PRP Process for culture purity, *H. influenzae* inactivation and PRP antigen content were all satisfactory.

Three lots of PRP prepared by the Enhanced Process were subsequently used in the manufacture of Haemophilus b Conjugate Vaccine (Meningococcal Protein Conjugate). The derivatized Haemophilus b polysaccharide bulk was subjected to complete control testing and all of the test results show that these materials from Enhanced Process PRP are indistinguishable from similar materials from the selective alcohol fractionation process.

Test results of the final container material confirm that the Haemophilus b Conjugate Vaccine (Meningococcal Protein Conjugate) prepared with PRP from the Enhanced Process is of the same quality as the product prepared from alcohol fractionated PRP.

What is claimed is:

1. A process for preparing lipid and endotoxin free capsular polysaccharide from a crude or purified preparation comprising both lipid-free and lipo-capsular polysaccharide, derived from bacteria, without substantial loss of the capsular polysaccharide, which comprises converting substantially all the lipo-capsular polysaccharide into lipid-free capsular polysaccharide by cleaving the lipid from the lipo-capsular polysaccharide, removing free lipid and endotoxin contaminants, and recovering the lipid-free capsular polysaccharide.

2. A process for preparing lipid and endotoxin free capsular polysaccharide from a crude or purified preparation comprising both lipid-free and lipo-capsular polysaccharide, derived from bacteria, without substantial loss of the capsular polysaccharide, which comprises converting substantially all the lipo-capsular polysaccharide into lipid-free capsular polysaccharide by cleaving the lipid from the lipo-capsular polysaccharide, removing free lipid and endotoxin contaminants, and recovering the lipid-free capsular polysaccharide wherein the lipid is cleaved from the lipo-capsular polysaccharide by a phospholipase.

3. The process of claim 2 wherein the capsular polysaccharide is derived from a culture of *Haemophilus influenzae* type b, *Neisseria meningitidis* (meningococcal) groups A, B, C, X, Y, W135 or 29E or *Escherichia coli* K1, K12, K13, K89, K92 or K100.

4. The process of claim 3 wherein the capsular polysaccharide is a mixture comprising PRP and lipo-PRP derived from a culture of *Haemophilus influenzae* type b.

5. The process of claim 4 which comprises treating the mixture comprising PRP and lipo-PRP with phospholipase D alone or in combination with phospholipase $A_2$ or phospholipase B in the presence of an organic phase comprising ether as an enzyme activator.

6. The process of claim 5 wherein the organic phase comprises a mixture of a first component of ether selected from ethyl-ether, butyl-ether of methyl-tert-butyl-ether, and a second component selected from methanol, ethanol, or hexane, wherein said first component and said second component are present in a ratio of between about 20:1 and 5:1.

7. The process of claim 6 wherein the phospholipase is derived from a non-mammalian organism.

8. The process of claim 7 which comprises treating the mixture comprising PRP and lipo-PRP with phospholipase D alone.

9. The process of claim 8 which comprises reacting the mixture comprising PRP and lipo-PRP with between about 0.01% and 10% on a weight basis of phospholipase D.

10. A process for preparing lipid-free and endotoxin-free polyribosyl ribitol phosphate, PRP, without substantial loss of PRP, which comprises reacting lipo-PRP present in a crude or purified preparation of polysaccharide derived from a culture of *Haemophilus influenzae* type b with phospholipase D at a ratio of about 0.3 weight-percent of phospholipase D to PRP, in a reaction mixture comprising an ether:organic solvent mixture at a concentration of between 30% and 60% of the reaction volume, wherein the organic is an ether, selected from diethyl-ether, butyl-ether, or methyl-tert-butyl-ether, in admixture with a second organic selected from hexane, ethanol, or methanol, in the presence of a detergent selected from deoxycholate or Triton X-100, present at a concentration of between 0.1% and 0.4%, with addition of about 0.1 to about 10 mM CaCl$_2$, in a buffer compatible with the afore-mentioned reagents at a pH between about 7.0 and 8.0, a temperature between about 20° C. and 45° C., for between about 30 minutes and about 4 hours.

11. The process of claim 10 wherein the ether:organic solvent mixture is a methyl-tert-butyl ether:ethanol mixture in a ratio of about 9:1, and the concentration of the mixture is about 50% of the reaction volume.

12. The process of claim 11 which further comprises phenol extraction of the PRP to remove proteinaceous contaminants, including the added phospholiphase D, and passage of the PRP, either before or after treatment with phospholipase D, through a hydrophobic adsorption step which does not adsorb PRP or lipo-PRP, to remove free lipids and endotoxin.

13. A process for preparing lipild-free PRP without substantial loss of PRP, which comprises the steps of:
   a) culturing *Haemophilus influenzae* type b in a suitable culture medium;
   b) killing the *Haemophilus influenzae* type b with thimerosal or phenol;
   c) clarifying the culture medium of killed *Haemophilus influenzae* type b;
   d) concentrating the clarified culture medium to obtain a workable volume;
   e) precipitating contaminants in the culture medium by adding ethanol to a final concentration of about 48% ethanol to obtain a supernatant containing PRP and a contaminant pellet which is discarded;
   f) precipitating the PRP by adding ethanol to a final concentration of about 61% to obtain a crude-PRP pellet;
   g) adding water to the PRP pellet to solubilize it, followed by adding calcium chloride to a final concentration of 1.0M;
   h) adding ethanol to a final concentration of 23% to obtain an insoluble pellet of contaminants and a supernatant containing the PRP;
   i) adding ethanol to a final concentration of 37% to precipitate the PRP;
   j) triturating the PRP pellet with absolute ethanol and drying to obtain a PRP pre-phenol powder;
   k) phenol extracting a solubilized preparation of the PRP powder;
   l) precipitating the PRP by adding CaCl$_2$ to 0.05M and alcohol to about 67%, triturating in absoulute ethanol to obtain post-phenol powder;
   m) removing endotoxin by hydropohobic adsorption from a solubilized preparation of post-phenol powder;
   n) reacting the PRP in crude-PRP, pre-phenol powder, or post-phenol powder, with a phospholipase, before proceeding with subsequent steps.

14. The process of claim 13 wherein the phospholipase is phospholipase D which is added at about 0.3 weight percent as compared to PRP, and the crude-PRP, pre-phenol powder, or post-phenol powder is solubilized in 10 mM Tris, 5 mM CaCl$_2$, 45% methyl tert butyl ether, 5% ethanol, 0.3% Triton X-100, and allowed to react at about 35° C. for 30 minutes to about 4 hours.

* * * * *